US009146200B2

(12) United States Patent
Zarra

(10) Patent No.: US 9,146,200 B2
(45) Date of Patent: Sep. 29, 2015

(54) SYSTEM AND METHOD FOR DETERMINING AN ORIENTATION OF RESERVOIR GEOBODIES FROM UNORIENTED CONVENTIONAL CORES

(71) Applicant: Larry Zarra, Houston, TX (US)

(72) Inventor: Larry Zarra, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 290 days.

(21) Appl. No.: 13/888,066

(22) Filed: May 6, 2013

(65) Prior Publication Data

US 2014/0328454 A1 Nov. 6, 2014

(51) Int. Cl.
| | |
|---|---|
| G06K 9/00 | (2006.01) |
| G01N 23/04 | (2006.01) |
| G01N 33/24 | (2006.01) |
| E21B 25/00 | (2006.01) |

(52) U.S. Cl.
CPC .............. *G01N 23/046* (2013.01); *G01N 33/24* (2013.01); *E21B 25/00* (2013.01)

(58) Field of Classification Search
None
See application file for complete search history.

(56) References Cited

U.S. PATENT DOCUMENTS

| | | | | |
|---|---|---|---|---|
| 4,306,810 | A | | 12/1981 | Maddox |
| 4,649,483 | A | * | 3/1987 | Dixon, Jr. ....................... 702/12 |
| 4,781,062 | A | | 11/1988 | Taylor |
| 4,868,883 | A | | 9/1989 | Chen |
| 5,109,398 | A | * | 4/1992 | Hunt et al. ..................... 378/208 |
| 5,277,062 | A | * | 1/1994 | Blauch et al. ............... 73/152.11 |
| 5,318,123 | A | * | 6/1994 | Venditto et al. ............ 166/250.1 |
| 5,331,155 | A | * | 7/1994 | Blauch ........................... 250/255 |
| 5,360,066 | A | * | 11/1994 | Venditto et al. ............ 166/250.1 |
| 6,393,906 | B1 | | 5/2002 | Vityk et al. |
| 6,473,696 | B1 | * | 10/2002 | Onyia et al. ....................... 702/6 |
| 6,704,436 | B1 | | 3/2004 | Anxionnaz et al. |
| 6,768,326 | B2 | * | 7/2004 | Brown et al. ............. 250/370.11 |
| 6,876,721 | B2 | * | 4/2005 | Siddiqui ......................... 378/52 |

(Continued)

FOREIGN PATENT DOCUMENTS

EP 0574237 12/1993

OTHER PUBLICATIONS

Hiscott, Richard N., "Paleoflow directions of Albian basin-floor turbidity currents in the Newfoundland Basin." *Proceedings of the Ocean Drilling Program, Scientific Results*. vol. 210. 2007 (http://www-odp.tamu.edu/publications/210_SR/VOLUME/CHAPTERS/103.PDF).

(Continued)

*Primary Examiner* — Jason Heidemann
(74) *Attorney, Agent, or Firm* — Albert K. Shung

(57) ABSTRACT

A system and method for determining an orientation of a reservoir feature from an unoriented core. The method includes selecting an arbitrary inclined plane in a longitudinal or transverse cross sectional CT scan image of the unoriented core; flattening the inclined plane by realigning all voxels within a volume of the unoriented core so as to obtain a horizontal plane in a realigned core; selecting a transverse cross sectional CT scan image of the realigned core where a desired feature is present; determining a correcting angle to be added to an angle of a flat-bed contact plane of the realigned core relative to a reference mark in the realigned core to obtain a correct inclination angle relative to compass map coordinates; determining a first angle between a direction perpendicular to the feature relative to the reference mark; and determining a second angle by adding the correcting angle to the first angle.

16 Claims, 14 Drawing Sheets

(56) References Cited

U.S. PATENT DOCUMENTS

| | | | |
|---|---|---|---|
| 6,984,983 | B2 | 1/2006 | Tabanou |
| 7,062,072 | B2 | 6/2006 | Anxionnaz et al. |
| 7,173,242 | B2 | 2/2007 | Liu et al. |
| 7,369,980 | B2 | 5/2008 | Deffenbaugh et al. |
| 7,769,545 | B2 | 8/2010 | Lomask et al. |
| 7,925,481 | B2 | 4/2011 | Van Wagoner et al. |
| 8,010,294 | B2 | 8/2011 | Dorn et al. |
| 8,068,579 | B1 * | 11/2011 | Yun et al. ............ 378/21 |
| 8,117,019 | B2 | 2/2012 | Sun et al. |
| 8,237,444 | B2 | 8/2012 | Simon |
| 8,736,600 | B2 * | 5/2014 | Lin et al. ............ 345/419 |
| 2011/0295580 | A1 * | 12/2011 | Sisk et al. ............ 703/10 |

OTHER PUBLICATIONS

Meyer, Cornelia, Michel Jebrak, Dieter Stoffler, Ulrich Riller, "Lateral transport of suevite inferred from 3D shape-fabric analysis: Evidence from the Ries impact crater, Germany," *Geological Society of America Bulletin* published online Aug. 19, 2011, doi: 10.1130/B30393.1 (http://gsabulletin.gsapubs.org/content/early/2011/08/19/B30393.1.full/pdf+html).

Pomar, L., M. Morsilli, P. Hallock, B. Badenas, "Internal waves, an under-explored source of turbulence events in the sedimentary record," Earth-Science Reviews, vol. 111, Issues 1-2, Feb. 2012, pp. 56-81 (Earth-Science Reviews, 111 (2012), 56-81).

Corbeanu, Rucsandra M, Michael C. Wizevich, Janok P. Bhattacharya, Xiaoxiang Zeng, and George A. McMechan, "Three-dimensional architecture of ancient lower delta-plain point bars using ground-penetrating radar, Cretaceous Ferron Sandstone, Utah." *The Fluvial-Deltaic Ferron Sandstone: Regional-to-Wellbore-Scale Outcrop Analog Studies and Applications to Reservoir Modeling* (2004) (http://nsmn1.uh.edu:2008/docs/geos/faculty-files/pdf/2001.pdf).

\* cited by examiner

0 DEG LONGITUDINAL

3"

90 DEG LONGITUDINAL

AXIAL

LOW X-RAY ATTENUATION    HIGH X-RAY ATTENUATION
-500.0                    3000.0

1540

1875

2075

0°
TOP

90°
SIDE

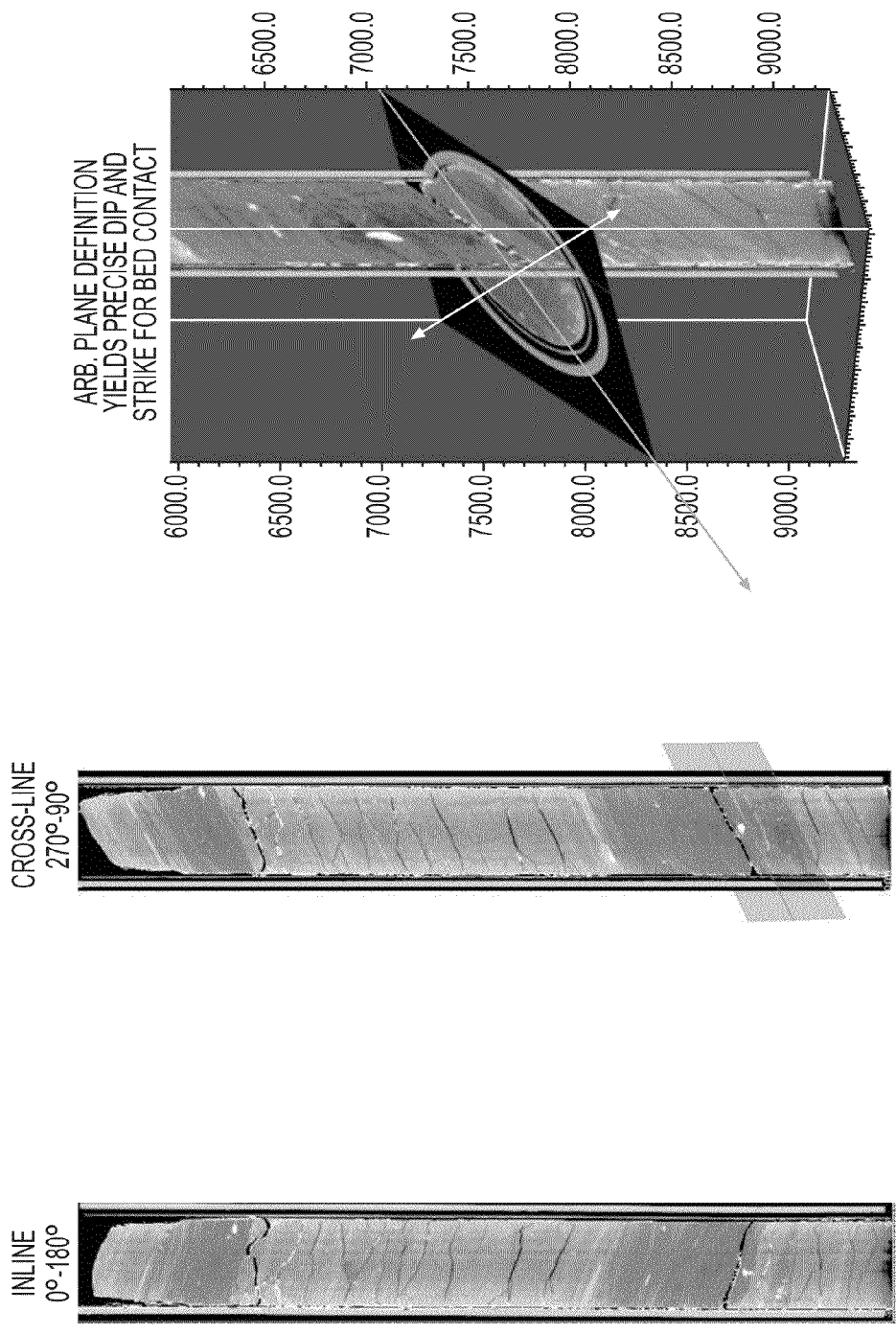

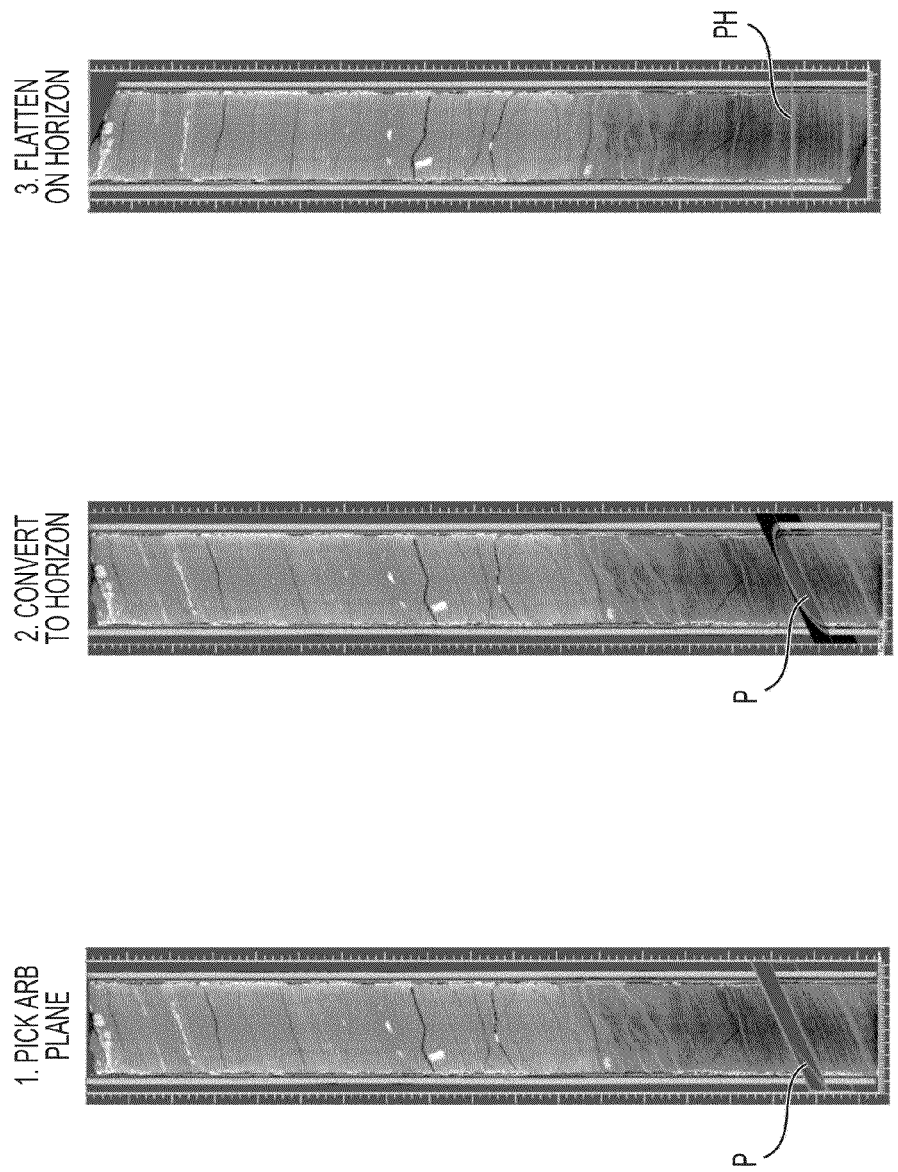

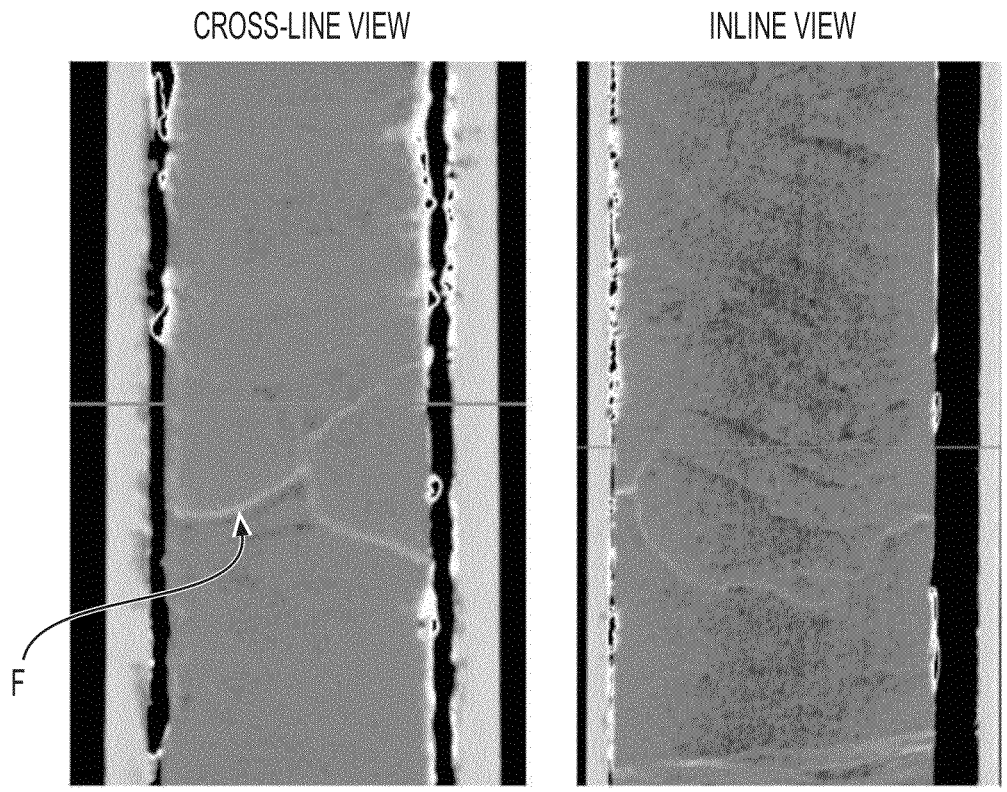
FIG. 14A  FIG. 14B
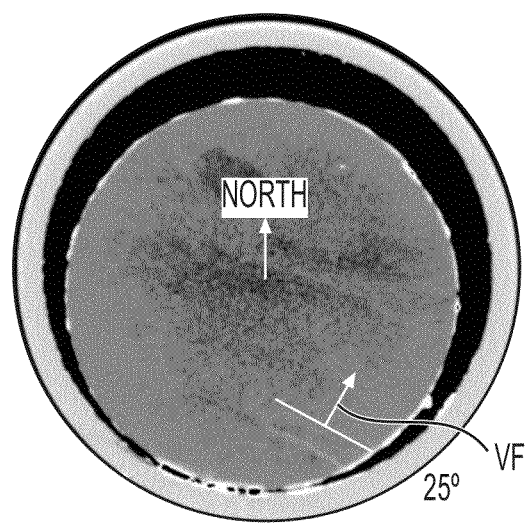
FIG. 14C

SYSTEM AND METHOD FOR DETERMINING AN ORIENTATION OF RESERVOIR GEOBODIES FROM UNORIENTED CONVENTIONAL CORES

FIELD

The present invention relates to a system and method for determining an orientation of reservoir geobodies from un-oriented conventional cores.

BACKGROUND

In the process of analyzing a rock formation, cores are often extracted to determine the composition of the rock formation in order to assess the oil or gas reservoir potential of the rock formation. The cores can be, for example, analyzed using a computed tomography (CT) scanner to determine the various layers of sediments present in the core. However, although various layers of sediments can be distinguished using a CT scanner, conventional cores are not oriented. A CT scanner is an imaging device that uses X-rays to produce tomographic images or 'slices' or cross sections of a specific area of a material. CT scanners are widely used in the medical field for diagnostics and therapeutic purposes. However, CT scanners can also be used in other fields such as nondestructive material testing or material imaging. The term "oriented" is used herein to define the geographical orientation or compass direction (i.e., East-West, North-South, etc.). Although the position or location and depth where the core is extracted are known, the orientation of the features or layers within the core relative to the compass direction is not known. For example, what can be extracted from the conventional un-oriented core is simply the presence or absence of a channel at a certain depth. However, it is not possible at the present time to determine which compass direction (e.g., east-west, north-south, etc.) the channel is oriented.

At the present time there are no methods or systems to extract the orientation of features or geobodies (e.g., channels) in the sedimentary layers of the rock formation from conventional un-oriented cores. Therefore, it would be highly desirable to provide a method and system for determining an orientation of reservoir geobodies such as channels or other features from un-oriented conventional cores.

SUMMARY

An aspect of the present invention is to provide a method for determining an orientation of a reservoir feature from an unoriented core from a subsurface. The method includes selecting an arbitrary inclined plane in a longitudinal or transverse cross sectional CT scan image of the unoriented core, the unoriented core being extracted from a borehole inclined relative to a vertical direction; flattening the inclined plane by realigning all voxels within a volume of the core so as to obtain a horizontal plane in a realigned core; selecting a transverse cross sectional CT scan image of the realigned core where a desired feature is present; determining a correcting angle to be added to an angle of a flat-bed contact plane of the realigned core relative to a reference mark in the realigned core to obtain a correct inclination angle relative to one or more compass map coordinates; determining a first angle between a direction perpendicular to the feature in the transverse cross sectional CT scan image relative to the reference mark; and determining a second angle of the direction perpendicular to the feature by adding the correcting angle to the first angle, the second angle corresponding to the angle of water flow or channel mapped to the compass coordinates.

Another aspect of the present invention is to provide a system for determining an orientation of a reservoir feature from an unoriented core from a subsurface. The system includes one or more processors configured to: (a) read data parameters of an arbitrary inclined plane in a longitudinal or transverse cross sectional CT scan image of the unoriented core, the unoriented core being extracted from a borehole inclined relative to a vertical direction; (b) flatten the inclined plane by realigning all voxels within a volume of the unoriented core so as to obtain a horizontal plane in a realigned core; (c) read a transverse cross sectional CT scan image of the realigned core where a desired feature is present; (d) determine a correcting angle to be added to an angle of a flat-bed contact plane of the realigned core relative to a reference mark in the realigned core to obtain a correct inclination angle relative to one or more compass map coordinates; (e) determine a first angle between a direction perpendicular to the feature in the transverse cross sectional CT scan image relative to the reference mark; and (f) determine a second angle of the direction perpendicular to the feature by adding the correcting angle to the first angle, the second angle corresponding to the angle of water flow or channel mapped to the compass coordinates.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 6A and 6B are longitudinal cross sectional views of a CT scan of a core in the inline direction (an arbitrary 0 deg. direction) and the cross-line (x-line) direction (an arbitrary 90 deg. direction), according to an embodiment of the present invention;

FIG. 6C is a longitudinal cross sectional view of a CT scan of a core in the cross-line direction provided within a 3D frame and showing an arbitrary plane representing the flatbed contact, the plane having an inclination or dip relative to an horizontal direction, according to an embodiment of the present invention;

FIG. 8A is a longitudinal cross sectional view of a CT scan of a core showing a location of a defined flat plane, according to an embodiment of the present invention;

FIG. 8B is a longitudinal cross sectional view of a CT scan of the core showing the plane from FIG. 8A wherein the plane is converted to horizon, according to an embodiment of the present invention;

FIG. 8C is a longitudinal cross sectional view of a CT scan of the core showing the vertical realignment of the pixel array in FIG. 8B relative to a flattened horizon, according to an embodiment of the present invention;

FIGS. 14A-14B are longitudinal cross sectional views: a cross-line view and an inline view, respectively, of a CT scan of a core, according to an embodiment of the present invention;

FIG. 14C is a transverse cross sectional view of a CT scan of the same core shown in FIGS. 14A and 14B.

DETAILED DESCRIPTION

Figure 1A:
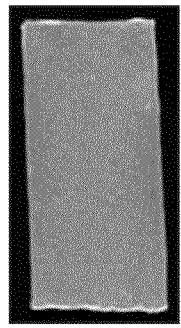
FIGS. 1A and 1B are examples of longitudinal cross section views, respectively at 0 deg. and 90 deg., of a CT scan of a core.
Figure 1B:
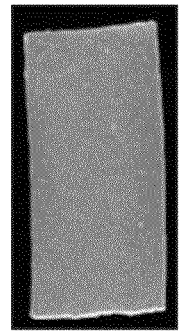
Figure 1C:
FIG. 1C is an example of a transverse cross-sectional view of the CT scan of the core.
Figure 2A:
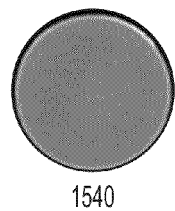
FIGS. 2A-2C are cross-sectional CT scan views of various cores containing different rock compositions.
Figure 2B:
Figure 2C:
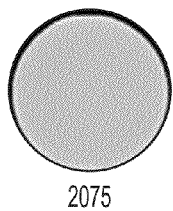

FIGS. 1A and 1B are longitudinal cross section views, respectively at 0 deg. and 90 deg., of a CT scan of a core. The 0 deg. direction is simply a reference taken on the core and is arbitrary. The 90 deg. direction is perpendicular to the 0 deg. direction. FIG. 1C is a transverse cross-sectional view of the CT scan of the core, according to an embodiment of the present invention. CT scans are measured in Hounsfield units. Hounsfield units (HU) are a measure of X-ray attenuation between a source and a receiver. X-ray attenuation is higher for denser rocks such as shale and cemented sandstone and lower for less dense rock such as porous sandstone. For example, the X-ray attenuation of air is approximately zero, the X-ray attenuation for water is approximately 1000 HU (Hounsfield Units) and the X-ray attenuation for sedimentary rock is in the range between about 1000 and about 3000 HU. FIGS. 2A-2C are cross-sectional CT scan views of various cores containing different rock compositions. FIG. 2A is a cross-sectional view of a CT scan with average X-ray attenuation value of about 1540 which indicates that the core contains sandstone. FIG. 2B is a cross-sectional view of a CT scan with an average X-ray attenuation of about 1875 indicating that the core contains a mixture of shales and sandstone. FIG. 2C is a cross-sectional view of a CT scan with an average X-ray attenuation of about 2075 indicating that the core contains shale.

Figure 3A:
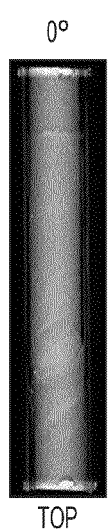
FIG. 3A is a longitudinal cross sectional view of a CT scan of a core in the 0 deg. direction, according to an embodiment of the present invention.
Figure 3B:
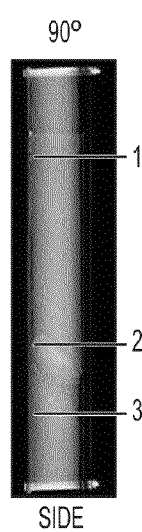
FIG. 3B is a longitudinal cross sectional view of a CT scan of a core in the 90 deg. direction, according to an embodiment of the present invention.

FIG. 3A is a longitudinal cross sectional view of a CT scan of a core in the 0 deg. direction. FIG. 3B is a longitudinal cross sectional view of a CT scan of a core in the 90 deg. direction. The 0 deg. direction is simply a reference taken on the core and is arbitrary. The 90 deg. direction is perpendicular to the 0 deg. direction. The lines 1, 2 and 3 indicate various depth positions in the core where a transverse cross sectional view of the core is visualized in the CT scan.

Figure 3C:
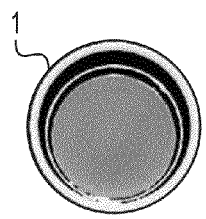
FIG. 3C is a transverse cross sectional view of the CT scan of the core taken at a first position, according to an embodiment of the present invention.
Figure 3D:
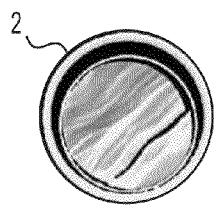
FIG. 3D is a transverse cross sectional view of the CT scan of the core taken at a second position, according to an embodiment of the present invention.
Figure 3E:
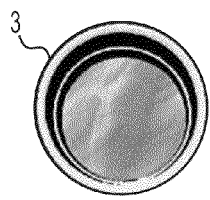
FIG. 3E is a transverse cross sectional view of the CT scan of the core taken at a third position, according to an embodiment of the present invention.

FIG. 3C is a transverse cross sectional view of the CT scan of the core taken at position 1. FIG. 3D is a transverse cross sectional view of the CT scan of the core taken at position 2. FIG. 3E is a transverse cross sectional view of the CT scan of the core taken at position 3. As can be seen in these three different transverse cross sectional views, cross sectional view 1 shows the lowest attenuation indicating that the core at this depth contains more sandstone than shale while the cross sectional 2 shows the highest attenuation indicating that the core at this depth contains more shale than sandstone.

Figure 4A:
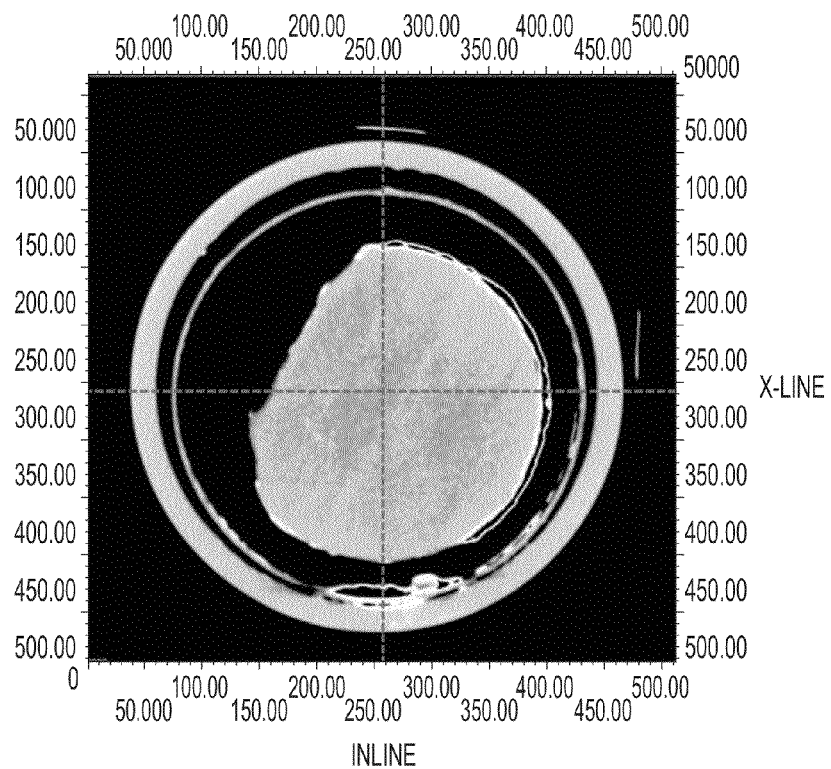
FIG. 4A is a transverse cross sectional view of a CT scan of a core, according to an embodiment of the present invention.

FIG. 4A is a transverse cross sectional view of a CT scan of a core, according to an embodiment of the present invention. In this embodiment, the CT scan is a helical CT scan. In a helical CT scan data is recorded at greater than 1000 slices per foot of core providing (in this instance) a voxel dimension of about 0.03 mm in the vertical direction and 0.39 mm in the horizontal. However, as it can be appreciated, data can also be recorded or acquired at a higher or lower number of slices resulting in a higher resolution or lower resolution in terms of voxels. As known in the art, a voxel ("volume pixel") is the counterpart imaging unity of a pixel but in a three-dimensional (3D) volume. As shown in FIG. 4A, reference markers are used to define the 0 deg. and the 90 deg. directions. These reference markers can be for example copper disks. The 0 deg. direction corresponds to the reference inline direction (a visual line used to mark the core) and the 90 deg. direction corresponds to the cross-line or X-line direction as shown in FIG. 4A.

Figure 4B:
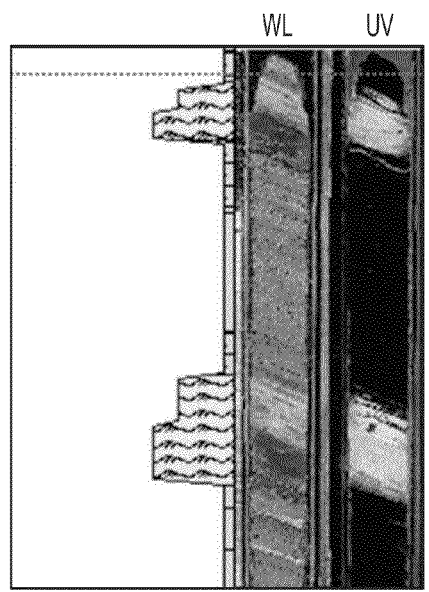
FIG. 4B is a longitudinal cross sectional view of the core inspected visually, according to an embodiment of the present invention.

FIG. 4B is a longitudinal cross sectional view of the core inspected visually, according to an embodiment of the present invention. The core is extracted at a desired depth (the length of the core being about 3 feet, for example). The longitudinal view on the left is a longitudinal view in the 0 deg. direction with the features within the core viewed under normal visible light or white light (WL). The longitudinal view on the right is a longitudinal view in the 0 deg. direction with the features within the core viewed under ultraviolet light (UV). The sandstone containing oil fluoresce yellow and is visible on the right longitudinal view as two tilted bars. A dotted line at the top of the core indicates the position or depth where the transverse cross sectional view shown in FIG. 4A is taken.

Figure 5:
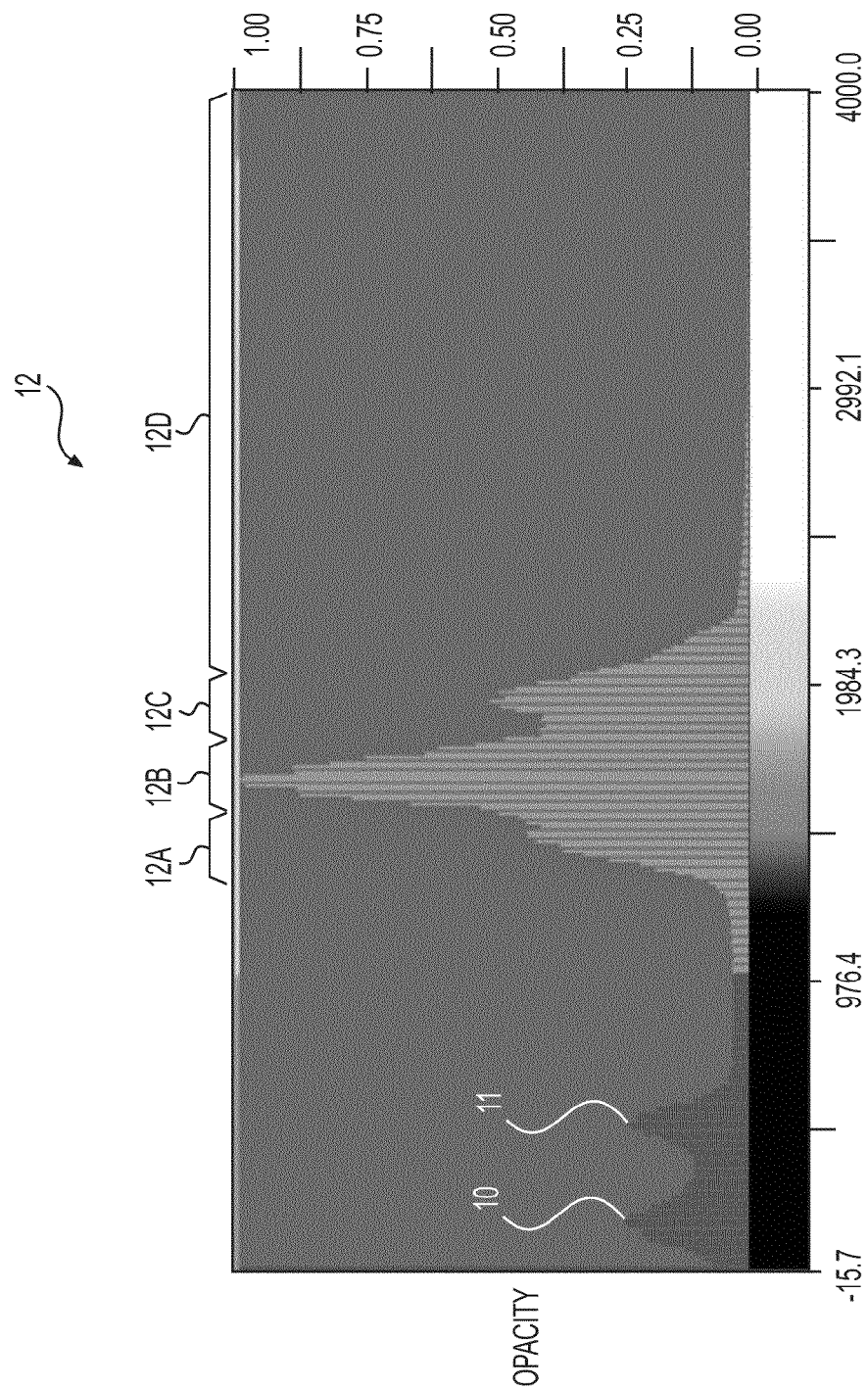
FIG. 5 is an example of a histogram of a frequency distribution of Hounsfield units in a helical CT scan data of a transverse cross-sectional slice taken from a core, according to an embodiment of the present invention.

FIG. 5 is an example of a histogram of a frequency distribution of Hounsfield units (HU) in a helical CT scan data of a transverse cross-sectional slice taken from a core, according to an embodiment of the present invention. The vertical axis of the histogram represents the cumulative frequency of measurements for a given range of HU values, and the horizontal axis represents the Hounsfield value. In this example, there are two relatively small peaks 10 and 11, one of which (peak 11) corresponds to epoxy used to stabilize the core and the other one (peak 10) represents null data. There is also present a relatively large peak 12 that has numerous maxima. For Hounsfield values in the range between about 1200 and about 1600, there is a first peak 12A that corresponds to sandstone. For Hounsfield values in the range between about 1600 and about 1800, there is a second peak 12B that corresponds to mudstone. For Hounsfield values in the range between about 1870 and about 1980, there is a third peak 12C that corresponds to the aluminum core tube, and mudstone. For Hounsfield values in the range between about 2000 and about 4000, there is minimal representation of high HU values (12D) that corresponds to mudstone, drilling mud solids, concretions and $CaCO_3$ cemented zones, siderite, and pyrite. In one embodiment, the helical CT scan data is output in SEG-Y format which can be rendered compatible with many geophysical software applications such as voxel-volume interpretation software VoxelGeo® from PARADIGM™ after conversion or manipulation (e.g., scaling, formatting, etc.). However, any suitable geophysical software applications may be used in conjunction with embodiments of the disclosed methods.

FIGS. 6A and 6B are longitudinal cross sectional views of a CT scan of a core in the inline direction (the 0 deg. direction) and the cross-line (x-line) direction (the 90 deg. direction), according to an embodiment of the present invention. The plane 20 shown in the x-line longitudinal cross sectional view corresponds to an arbitrary plane defined at a flat bedded contact. In this embodiment, the flat bed contact (virtual contact with the seabed) has a dip azimuth of 296 deg. relative to the inline direction or zero direction of the core which can be pointing to any compass direction. FIG. 6C is a longitudinal cross sectional view shown in FIG. 6B provided within a 3D frame and also shown is the inclination or dip of the plane 20 representing the flatbed contact with a dip azimuth of 296 deg.

Figure 7B:
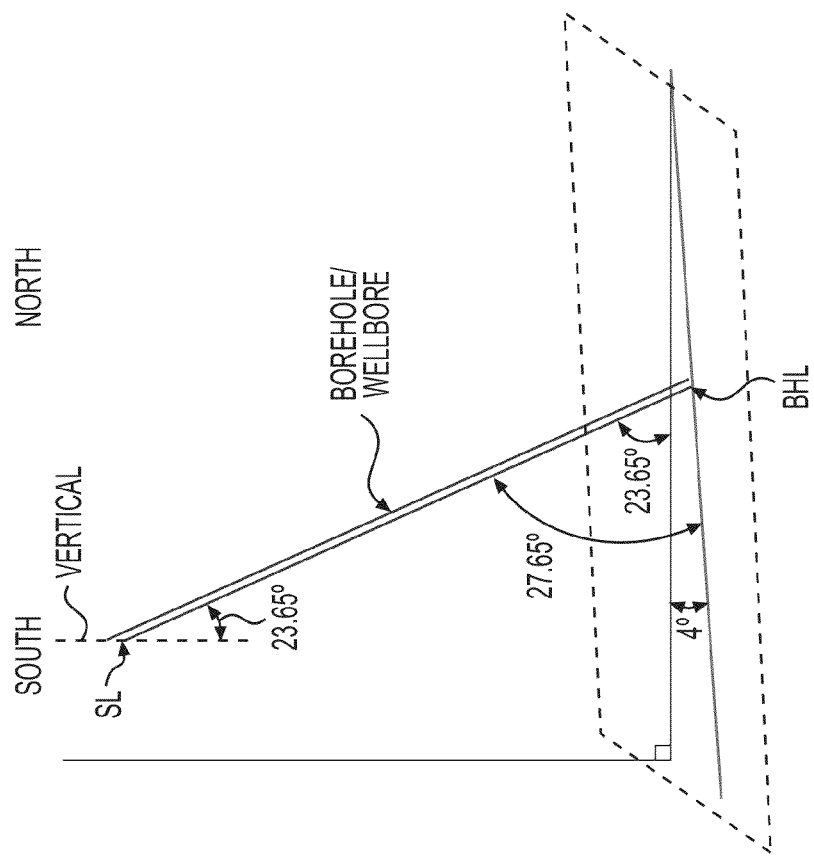
FIG. 7B shows a geometrical configuration of the wellbore or borehole relative to the vertical direction, according to an embodiment of the present invention.
Figure 7A:
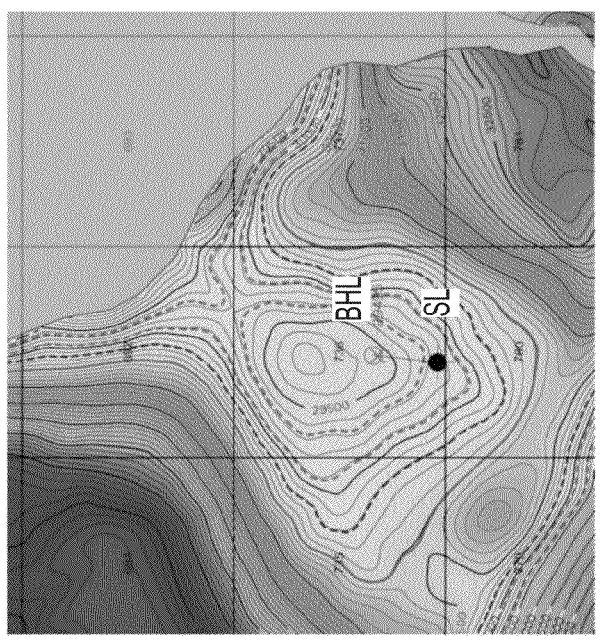
FIG. 7A is a contour map showing a location and orientation of a borehole or well bore from which the core shown in FIGS. 6A-6C is extracted, according to an embodiment of the present invention.

FIG. 7A is a structure contour map showing a location and orientation of a borehole or well bore from which the core shown in FIGS. 6A-6C is extracted, according to an embodiment of the present invention. The black dot represents the surface location (SL) of the well and the open dot or circle is the bottom hole location (BHL) of the well. As shown in FIG. 7A, the well or borehole is generally drilled from south to north. FIG. 7B shows a geometrical configuration of the wellbore or borehole relative to the vertical direction, according to an embodiment of the present invention. The borehole has an inclination of 23.65 deg. relative the vertical direction (the vertical direction being at 0 deg. inclination). In addition, the interval being cored is not flat and is essentially inclined to the south, south-east by approximately 4 deg. Therefore, the core would reflect a combination of the 23.65 deg. and the 4 deg. inclinations to have an inclination of approximately 27.65 deg., as illustrated in FIG. 7B. In other words, beds that were deposited flat on the seabed, for example, are inclined in the core by about 27.65 deg., as a result of borehole deviation or inclination of 23.65 deg. and structural dip of the formation of about 4 deg.

From reading the map the rock formation dip azimuth may be determined at the well bottom hole location to be 140 deg. The dip azimuth is measured from the well BHL on the map in a direction that is perpendicular to the nearest down-structure map contours, in this case, approximately 140 deg. As stated in the above paragraphs, with respect to the core description, the flat bed contact has a dip azimuth of 296 deg. relative to the inline direction of the core (measured from the plane of the core). However, as stated above, in other embodiments, it is contemplated that the inline or 0 deg. direction of the core can be pointing to any compass direction. Nevertheless, in the example shown in FIG. 7A, it is interpreted from the map that the flat bed dip azimuth direction should be pointing to 140 deg. Therefore, in order to obtain the correct azimuth dip angle of 140 deg. from the observed azimuth dip angle of 296 deg., a rotation angle α is added to the azimuth dip angle of the core plane of 296 deg. (296 deg.+α=360 deg.+140 deg.). Therefore, in this instance, the rotational or azimuth dip correction angle α is 204 deg. so that the features in the core are oriented to real world compass coordinates (i.e., map coordinates).

In the following paragraphs, a method for orienting core features relative to a real map is described. In one embodiment, the method starts by selecting an arbitrary inclined plane in a core. In an embodiment, the disclosed methods may be performed using any suitable geophysical analyses software packages known to those of skill in the art. FIG. 8A is a longitudinal cross sectional view of a CT scan of a core, according to an embodiment of the present invention. FIG. 8A shows an arbitrary inclined plane P that is selected within the longitudinal cross sectional view of the CT scan of the core. In this context, an arbitrary plane has its spatial configuration defined by 3 points in the interpretational space. FIG. 8B is a longitudinal cross sectional view of a CT scan of the core wherein the arbitrary plane, P, is converted to a horizon. In this context, a horizon is defined by specifying all points in a voxel volume coincident with a specified plane. An arbitrary plane can be converted to a horizon as the result of additional specific delineations and operations provided within the geophysical software package (e.g., VoxelGeo®). The purpose for converting an arbitrary plane to a horizon is to allow subsequent volume wide operations to be conducted relative to a horizon. In this case a simple 3-point surface is used for illustrative purposes. The operation and procedure is also valid for non-linear planes that have no repeated Z (depth) values. Next, the voxel volume represented by the longitudinal cross sectional view (FIG. 8B) is flattened relative to the horizon. In this flattening operation, the surface P is rendered horizontal from its originally inclined position, which also results in the entire 3 dimensional voxel array having the vertical position of contained voxels realigned to allow the inclined surface P to become entirely horizontal, as surface PH. The application of converting to horizon and flattening to horizon of a core or core orientation is new. FIG. 8C is a longitudinal cross sectional view of a CT scan of the core where the originally inclined plane is flattened. In flattening the plane P, the flattening vertically realigns all of the voxels in that volume. A new volume is created where all of the voxels are moved vertically in the sense that it allows the inclined plane P to be a flat plane PH. In flattening, the x and y position of the voxels in the plane do not change. However, the position of the voxels in the z direction is changed so that the voxels within the CT scan volume all have the same relative spacing relative to the plane PH.

A surface that is assumed to have been deposited flat on the sea bottom but appears inclined in the core, due to the angle of the borehole relative to the vertical direction and also due to post-deposit depositional structuring in the subsurface, can be flattened using the above described flattening operation to restore the original depositional flatness. As a result, the structural imprint from the borehole deviation or inclination and from the structural imprint from the incline of the bed in the subsurface can be corrected. In this way, a core with flat deposited sedimentary features can be obtained. By analyzing the orientation of the sedimentary features within the original depositional bed, it is possible to determine the paleocurrent direction which the grains were flowing or the water was flowing that deposited the sedimentary features. An analogy can be made with a river or a water flow channel. If dunes or ripples are found in the river bed, the ripples are more likely to be pointing in the direction that the water is flowing. Hence, if the direction of the flow can be measured from the ripples, then the pointing direction of the channel can be determined.

Figure 9B:
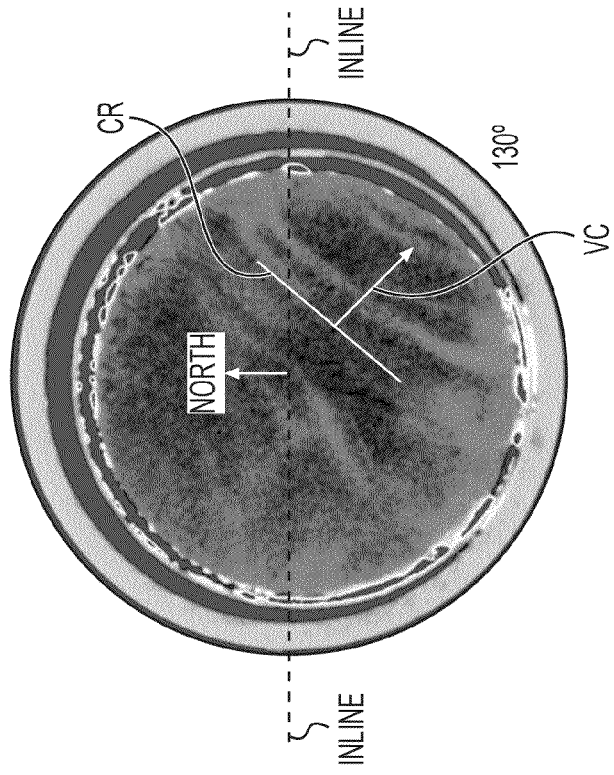
FIG. 9B is the transverse cross section taken at a plane PS shown in FIG. 9A, according to an embodiment of the present invention.
Figure 9A:
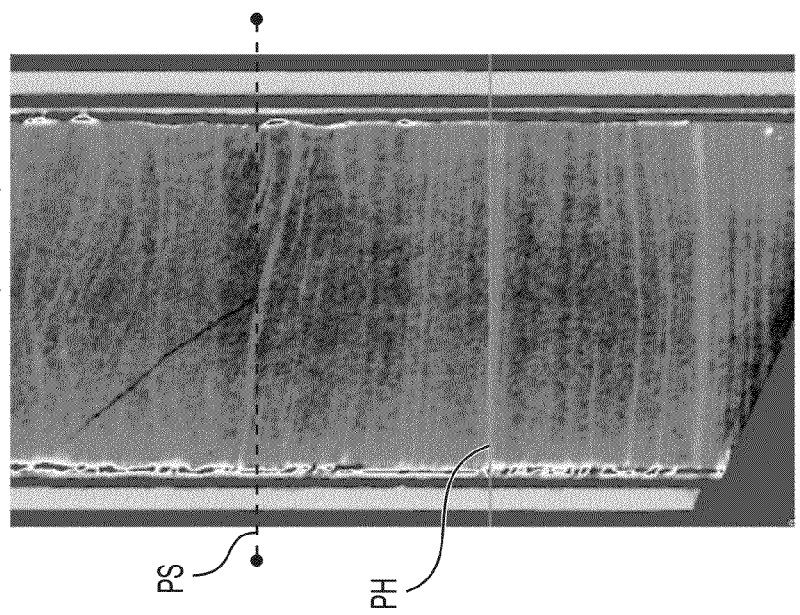
FIG. 9A is a flattened longitudinal cross sectional view of a core CT scan, according to an embodiment of the present invention.

FIG. 9A is a flattened longitudinal cross sectional view of a core CT scan, according to an embodiment of the present invention. The flat plane PH is shown in FIG. 9A. A transverse cross sectional view of the core CT scan is taken at selected plane PS. FIG. 9B is the transverse cross section taken at plane PS. The transverse cross section is a slice within a volume of CT data. In one embodiment, each slice is a 512 pixels by 512 pixels image. In one embodiment, one thousand of such slices can be obtained from approximately one vertical foot of core. However, as it can be appreciated a higher number of slices can also be obtained by increasing the resolution of the CT scan apparatus. The transverse cross section or slice can be performed so as to determine the direction of water flow during the deposition or sedimentary stage. As stated in the above paragraphs, this can be determined by looking at orientations of features such as a ripple within a slice of the core CT scan data. For example, the steepest direction of a ripple can indicate the direction of water flow (or paleodirection) and hence the direction of the channel.

For example, as shown in FIG. 9B, a line CR can be drawn in the general direction of a ripple or crest observed in the transverse cross sectional view of the core CT scan. A vector VC perpendicular to the line CR can then be drawn. The vector VC indicates the direction of water flow that created the ripple or crest CR. In this instance, the angle of the vector VC relative to the reference marker inline axis "INLINE" is equal to about 130 deg. As described in the above paragraphs, in order to map the core to the correct dip azimuth angle of 140 deg. of the geographical or compass coordinates, a correction angle α (e.g., equal to 204 deg.) is added to the initial dip azimuth angle 296 deg. Therefore, using the correction angle, the correct orientation of the feature (e.g., the ripple or crest) and thus the correct direction of the channel relative to real coordinates or compass coordinates can be obtained by adding to the angle of 130 deg., extracted from the core, to the correction angle 204 deg. (the correct angle of feature relative to compass coordinates=130 deg.+204 deg.=334 deg.). Hence, the corrected ripple or crest foreset direction is approximately 334 deg. With the corrected direction, the ripple or crest and thus the flow channel that created the ripple can be positioned correctly on the geographical map or compass coordinates.

One benefit provided by such method of positioning geo-features or geobodies (ripple, channel, etc.) in real coordinates or compass coordinates is to develop better reservoir models. This method can also be used for positioning subsequent drills or borehole, for example, to confirm the direction of the geo-features (e.g., channels, etc.) to enhance the reservoir models.

In the above paragraphs, the method is described while referring to a specific example with specific angles. However, as it can be appreciated, the present method is not limited to the above example. Indeed, the method encompasses any situation, feature or angle. Furthermore, in the above paragraphs, the method is described with reference to a ripple. In the following paragraph other examples are provided where the geo-features are cross beds. Cross beds are relatively large ripples (megaripples) or dunes that are deposited during water flow in a channel. A ripple is a feature that is, for example, about an inch tall and the spacing from ripple crest to ripple crest is about one foot. On the other hand, a cross bed or dune is a feature that is, for example, about a foot to two feet high with a spacing between two dunes of about five to ten feet or more. A cross bed is what's left after a dune migrates down flow in a channel. A cross bed is a sedimentary feature that forms when water flows over sediment and carries sediment. Cross beds can be more accurate indicators in which direction water was flowing that formed the cross beds.

Although a river is sometimes referred to herein by analogy to illustrate the method, as it can be appreciated the method is generally applicable to paleoflow determination where features are moving. In the deep sea there are channels cut that transport sediment across the continental shelf and slope out to the basin floor in some cases hundreds of miles. The sediments are called turbidites. A turbidite is a cloud or plume of sediment transported down a slope under gravity. The turbidite is traveling under its own density contrast down slope because the turbidity cloud is denser than the water that is surrounding it.

Figure 10:
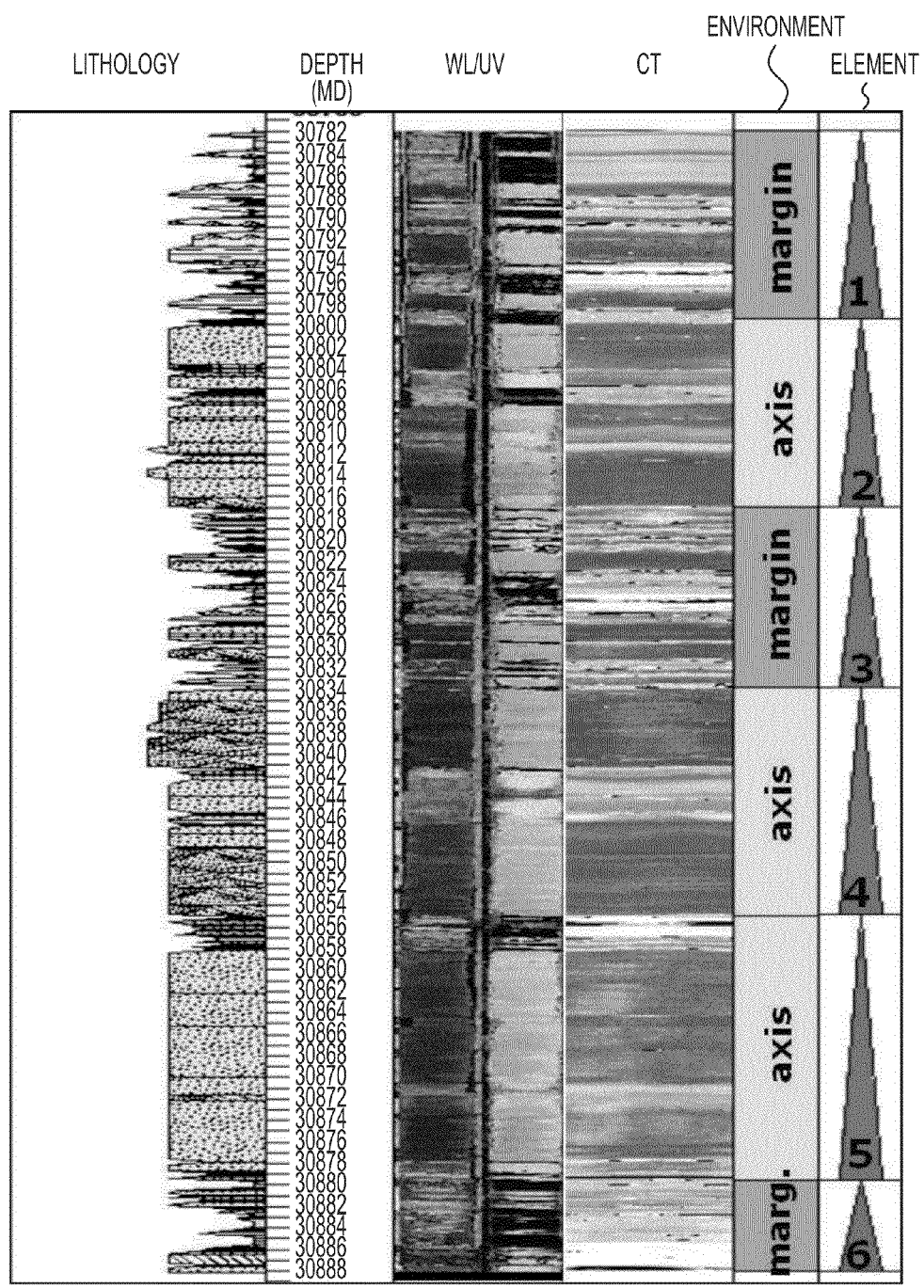
FIG. 10 depicts lithology, white light, ultraviolet light and CT scan of an example of a longitudinal cross-sectional view of a core, according to an embodiment of the present invention.

FIG. 10 depicts lithology, white light, ultraviolet light and CT scan of an example of a longitudinal cross-sectional view of a core, according to an embodiment of the present invention. In this example, the core is about 106 feet long. The core can be, for example, broken into three-foot sections or shorter sections that have consistent orientation to the bedding of the strata within that rock. The first column labeled "lithology" represents the lithology of the core or the different kind of sandstones and shales (i.e., lithofaces) as described visually by a geologist. The next column labeled "WL" shows photographs of the core under white light, and the column labeled "UV" shows photographs of the core under ultraviolet light. The column labeled "CT" shows the longitudinal view of CT scans of the core. The orange areas in the CT scan correspond to the sandstones and the yellow areas correspond to the shales. In the "environment" column, the core is divided into three yellow blocks which are interpreted to represent channel axis elements and three green blocks that are interpreted to represent channel margin elements. An element corresponds to a series of rocks that are related. In terms of the river analogy, the yellows correspond to the sediments deposited in the middle of the river or "axis" where the flow of water is faster and the greens correspond to sediments that accumulate on the bank or "margin" where the flow of water is slower. On the right-most column, there are a series of triangles numbered from 1 to 6. Each triangle corresponds to an "axis" zone or element or a "margin" zone or element. Paleo-current information can be extracted from some of these 6 elements or zones. That is, rocks within each element may provide information on the direction in which the water is flowing.

For example, element 2 which corresponds to an "axis" element, contains mostly sandstone shown on the CT scan longitudinal cross sectional view as orange areas. However, element 2 contains also a little bit of shale shown on the CT scan cross sectional view as yellow areas (around the middle of element 2). Within this interval or element 2, six cross beds are measured.

Figure 11:
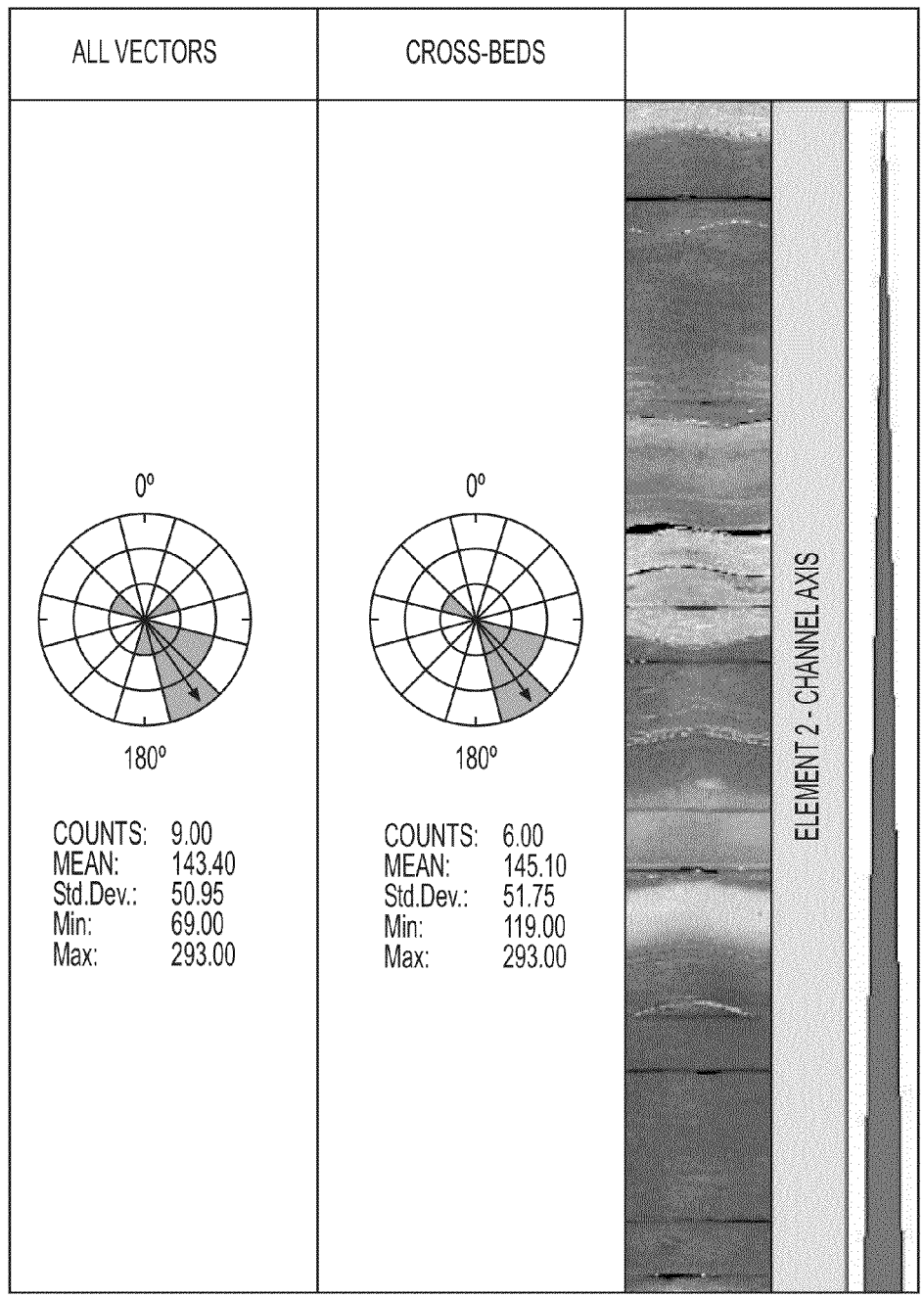
FIG. 11 depicts the results of the analysis of element 2 in the core, according to an embodiment of the present invention.

FIG. 11 depicts the results of the analysis of element 2 in the core, according to an embodiment of the present invention. The element 2 has 9 paleo-flow indicators: six cross beds, 2 flames and 1 imbricated clast. A rose or circular histogram can be constructed to indicate the orientation of all 9 paleo-flow indicators (the rose histogram on the left column in FIG. 11) and the orientation of only the 6 cross beds (the rose histogram on the right column in FIG. 11). In the rose histogram, the wedged slices are 30 degrees and the concentric circles are in percentages, in 10 percent. As shown in the right rose histogram corresponding to the six cross beds, 5 of the 6 vectors corresponding to the direction of the cross beds are pointing in the same direction and only one is pointing in the exact opposite direction. If 5 cross bed orientation are averaged, a mean of about 145 deg. can be obtained.

Therefore, the sandstone that is deposited by the water flow as a dune or cross bed is pointing in a compass direction of about 145 deg. In addition, most of the cross-beds (5 cross beds in this case) measured are pointing in the same direction which is in average 145 deg. The sixth measurement which points to the opposite direction is not due to a measurement error or indicative of a problem and is in fact reinforcing the fact that the cross beds are oriented in the general direction of 145 deg. indicating that a flow of water occurred in that direction. Indeed, a cross bed or dune is a three-dimensional feature. A cross bed generally has a steep side and shallow side. The shallow side is the side where water is coming and the steep side is the side where water is leaving the dune. Therefore, the 5 cross beds that are measured pointing in the same direction are measurement taken from the front side of the cross beds whereas the cross bed that is pointing in the opposite direction corresponds to a measurement taken from a back side of a cross bed thus the opposite direction.

Figure 12:
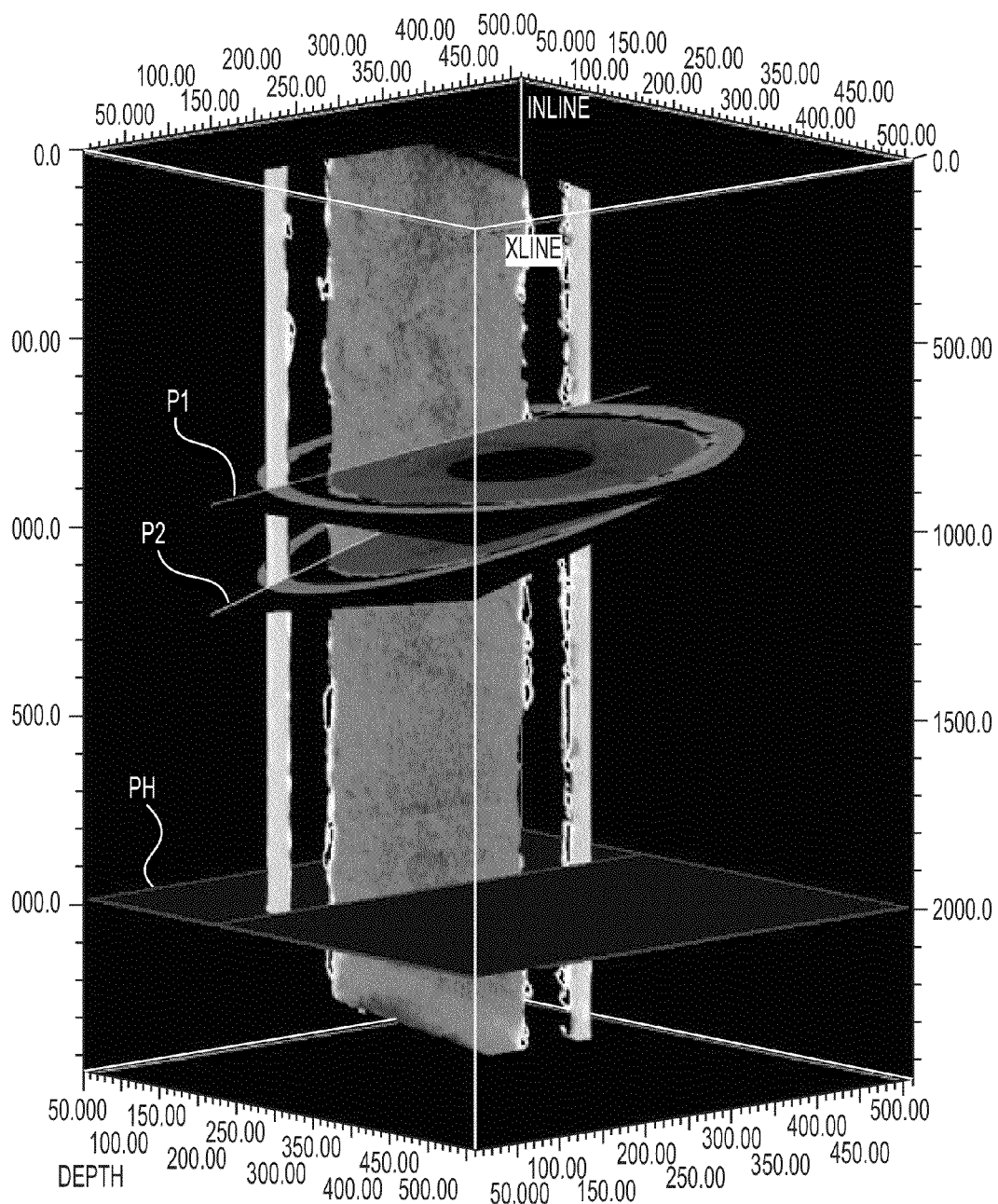
FIG. 12 is another example of a longitudinal cross sectional view of a CT scan of a portion of a core, according to an embodiment of the present invention.

FIG. 12 is another example of a longitudinal cross sectional view of a CT scan of a portion of a core, according to an embodiment of the present invention. Two cross beds can be observed in this longitudinal cross section. These two cross beds are represented by two planes P1 and P2. The plane PH corresponds to the horizontal plane that is used to perform the flattening operation, as described in detail in the above paragraphs. Plane P1 corresponds to a cross bed that is dipping or is inclined at an angle of about 4 deg. Plane P2 corresponds to a cross bed that is dipping or is inclined at an angle of about 14 deg. Plane P1 is at a corrected dip azimuth of about 141 deg., corrected using the correction angle 209 deg. Plane P2 is at a corrected dip azimuth of about 155 deg., also corrected using the correction angle 209 deg. These two cross beds are essentially pointing in the same direction (southeast). Therefore, it can be said that, on average, a channel of water carrying sedimentary particles that created the two cross beds was flowing in the general direction of 141 deg. to 155 deg. (southeast) in the compass coordinates.

Figure 13:
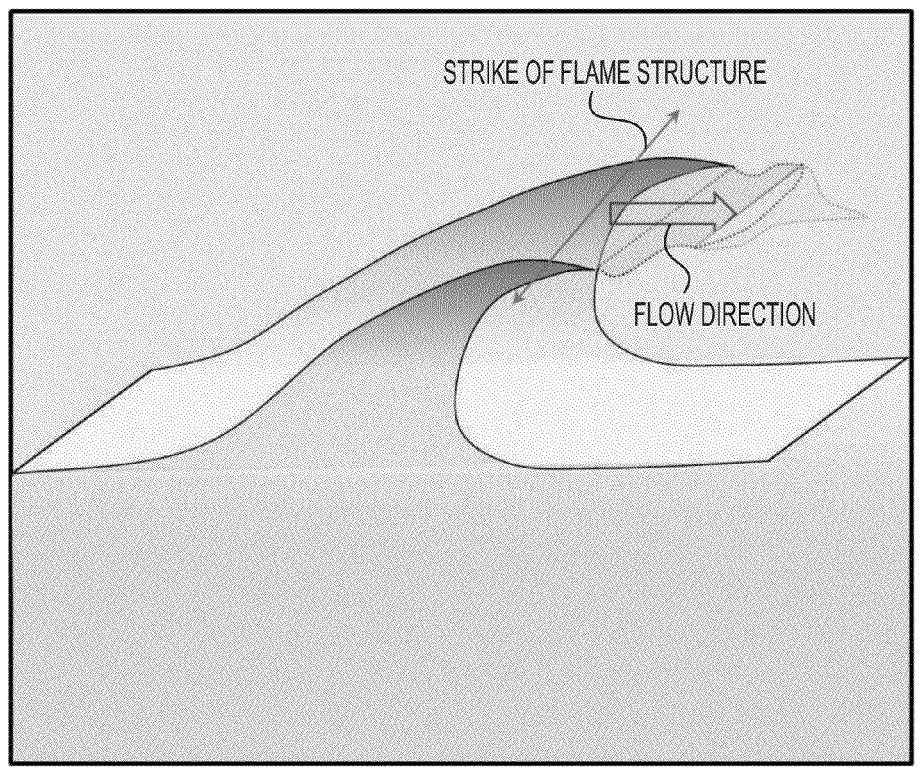
FIG. 13 depicts a schematic three-dimensional representation of a flame structure, according to an embodiment of the present invention.

FIG. 13 depicts a schematic three-dimensional representation of a flame structure, according to an embodiment of the present invention. A flame structure is a sedimentary structure that usually consists of upward-pointing flame-shaped finer-grained sedimentary wedge that protrudes into coarser sediment (e.g., sand). Almost invariably, the flame is inclined in a downflow direction (in a paleogeographic sense). A flame structure forms as the upper sandy layer part sinks into the underlying muddy sediment often referred to as "loading". The directional component of the tip of the flame is produced due to some current strength which shears the loaded material just slightly in a down flow direction before everything comes to rest as a deposit. The flow direction (indicated in FIG. 13 by an arrow) that deposited the flame structure is usually normal to the crest or strike of the flame (indicated in FIG. 13 by a double arrow line).

FIGS. 14A-14B are longitudinal cross sectional views, a cross-line view and an inline view, respectively, of a CT scan of a core, according to an embodiment of the present invention. A flame structure F is visible on the cross-line longitudinal view of the CT scan of the core.

FIG. 14C is a transverse cross sectional view of a CT scan of the same core shown in FIGS. 14A and 14B. On the transverse cross sectional view is shown the vector or direction VF of the flame tip. The direction of the vector is triangulated from cross-line and inline views shown in FIGS. 14A and 14B, respectively. The apparent flame tilt direction is about 25 deg. (measured in the cross-line view). The map dip azimuth is 140 deg. The dip azimuth obtained from the analysis of the core is 2 deg. Therefore, the correction angle α dip azimuth to the map can be obtained using the following equation (2 deg.+α=140 deg.) which provides a correction angle of about 138 deg. Using the correction angle of 138 deg., the flame tilt direction of 25 deg. can be corrected to the map or compass coordinates to obtain a corrected flame tilt direction of about 163 deg.

As it can be appreciated, additional techniques can be developed for determining paleo-flow direction by interpreting various primary sedimentary depositional features. For example, the flat axes of imbricated clasts can be interpreted to point up-flow. In another example, tool, flute, or scour marks on bed interfaces can also be interpreted to indicate directionality.

As it can be appreciated from the above paragraphs, a method for determining an orientation of a reservoir feature from an unoriented core from a subsurface is provided. The method includes 1) selecting an arbitrary inclined plane in a longitudinal or transverse cross sectional CT scan image of the unoriented core, the unoriented core being extracted from a borehole inclined relative to a vertical direction; 2) flattening the plane by realigning all voxels within a volume of the unoriented core so as to obtain a horizontal plane in a realigned core; 3) selecting a transverse cross sectional CT scan image of the realigned core where a desired feature is present; 4) determining a correcting angle to be added to an angle of a flat-bed contact plane of the realigned core relative to a reference mark in the realigned core to obtain a correct inclination angle relative to one or more compass map coordinates; 5) determining a first angle between a direction perpendicular to the feature in the transverse cross sectional CT scan image relative to the reference mark; and 6) determining a second angle of the direction perpendicular to the feature by adding the correcting angle to the first angle, the second angle corresponding to the angle of water flow or channel mapped to the compass coordinates.

In one embodiment, the selecting of the arbitrary inclined plane in the CT scan image of the core comprises selecting an inclined plane corresponding to a surface of a layer within the unoriented core that is assumed to have been deposited flat on a bottom of a seabed but appearing inclined in the unoriented core due to borehole inclination angle and post-depositional structuring in the subsurface. In one embodiment, the feature includes a sedimentary feature. For example, the sedimentary feature may include a ripple, a cross bed, or a flame, or any combination thereof.

In one embodiment, the method further includes repeating determining the first angle for a plurality of features with the core; and determining the second angle for the plurality of features within the core to obtain a plurality of second angles.

The method further includes, determining a statistical average of the plurality of second angles, wherein the statistical average of the second angles is indicative of an average direction of flow of water in a channel in compass map coordinates.

In one embodiment, the selecting of an arbitrary inclined plane in a longitudinal cross sectional CT scan image of the core includes selecting an arbitrary inclined plane in a longitudinal sectional helical CT scan image of the core. In one embodiment, the determining of the correcting angle to be added to the angle of the flat-bed contact plane of the core relative to the reference mark in the core includes determining a correcting angle relative to compass map coordinates.

In one embodiment, the method or methods described above can be implemented as a series of instructions which can be executed by a computer, the computer having one or more processors. As it can be appreciated, the term "computer" is used herein to encompass any type of computing system or device including a personal computer (e.g., a desktop computer, a laptop computer, or any other handheld computing device), or a mainframe computer (e.g., an IBM mainframe), or a supercomputer (e.g., a CRAY computer), or a plurality of networked computers in a distributed computing environment.

For example, the method(s) may be implemented as a software program application which can be stored in a computer readable medium such as hard disks, CDROMs, optical disks, DVDs, magnetic optical disks, RAMs, EPROMs, EEPROMs, magnetic or optical cards, flash cards (e.g., a USB flash card), PCMCIA memory cards, smart cards, or other media.

Alternatively, a portion or the whole software program product can be downloaded from a remote computer or server via a network such as the internet, an ATM network, a wide area network (WAN) or a local area network.

Alternatively, instead or in addition to implementing the method as computer program product(s) (e.g., as software products) embodied in a computer, the method can be implemented as hardware in which for example an application specific integrated circuit (ASIC) can be designed to implement the method.

Various databases can be used which may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Standard Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

Figure 15:
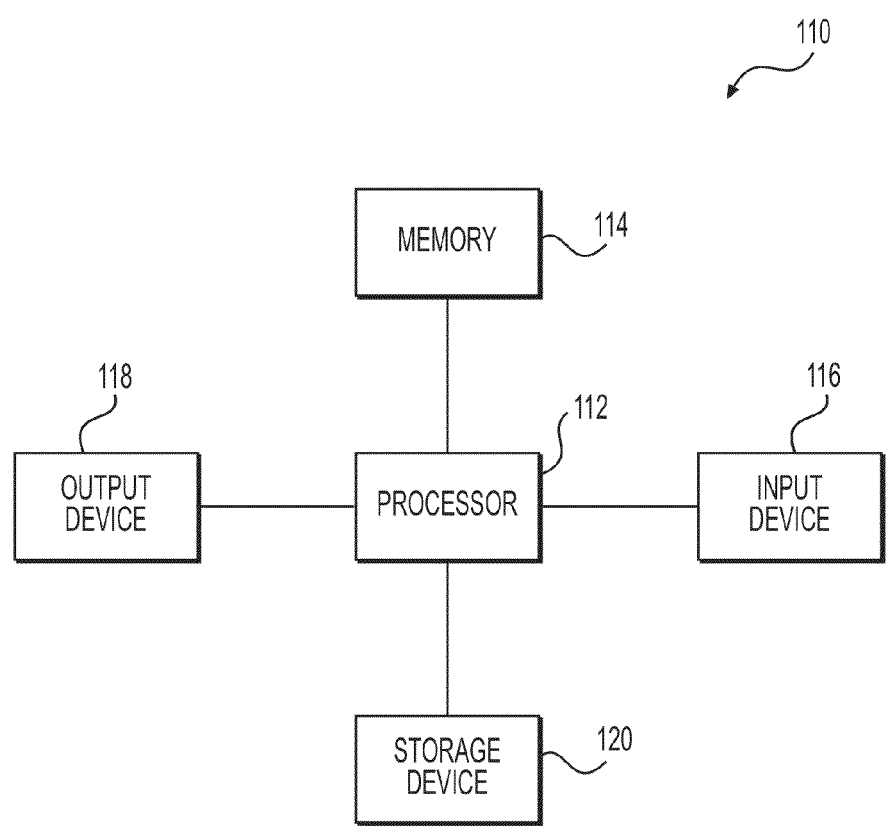
FIG. 15 is a schematic diagram representing a computer system for implementing the methods, according to an embodiment of the present invention.

FIG. 15 is a schematic diagram representing a computer system 110 for implementing the methods, according to an embodiment of the present invention. As shown in FIG. 15, computer system 110 comprises a processor (e.g., one or more processors) 112 and a memory 114 in communication with the processor 112. The computer system 110 may further include an input device 116 for inputting data (such as keyboard, a mouse or the like) and an output device 118 such as a display device for displaying results of the computation. The computer may further include or be in communication with a storage device 120 for storing data such as, but not limited to, a hard-drive, a network attached storage (NAS) device, a storage area network (SAN), etc. It must be appreciated that the term processor is used herein to encompass one or more processors. Where reference is made to a processor that term should be understood to encompass any of these computing arrangements.

As it can be appreciated from the above paragraphs, the system 100 is provided for determining an orientation of a reservoir feature from an unoriented core from a subsurface. The system 100 includes one or more processors 112 that are configured to (a) read data parameters of an arbitrary inclined plane in a longitudinal or transverse cross sectional CT scan image of the unoriented core, the unoriented core being extracted from a borehole inclined relative to a vertical direction. The data parameters include for example an inclination angle of the plane relative to a longitudinal axis of the core. The CT scan image data can be for example stored in a storage device 120. The one or more processors 112 are further configured to (b) flatten the inclined plane by realigning all voxels within a volume of the unoriented core so as to obtain a horizontal plane in a realigned core; (c) read a transverse cross sectional CT scan image of the realigned core where a desired feature is present; (d) determine a correcting angle to be added to an angle of a flat-bed contact plane of the realigned core relative to a reference mark in the realigned core to obtain a correct inclination angle relative to one or more compass map coordinates; (e) determine a first angle between a direction perpendicular to the feature in the transverse cross sectional CT scan image relative to the reference mark; and (f) determine a second angle of the direction perpendicular to the feature by adding the correcting angle to the first angle, the second angle corresponding to the angle of water flow or channel mapped to the compass coordinates.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Furthermore, since numerous modifications and changes will readily occur to those of skill in the art, it is not desired to limit the invention to the exact construction and operation described herein. Accordingly, all suitable modifications and equivalents should be considered as falling within the spirit and scope of the invention.

What is claimed is:

1. A method for determining an orientation of a reservoir feature from an unoriented core from a subsurface, comprising:

selecting an arbitrary inclined plane in a longitudinal or transverse cross sectional CT scan image of the unoriented core, the unoriented core being extracted from a borehole that is inclined relative to a vertical direction;

flattening the inclined plane by realigning all voxels within a volume of the core so as to obtain a horizontal plane in a realigned core;

selecting a transverse cross sectional CT scan image of the realigned core where a desired feature is present;

determining a correcting angle to be added to an angle of a flat-bed contact plane of the realigned core relative to a reference mark in the realigned core to obtain a correct inclination angle relative to one or more compass map coordinates;

determining a first angle between a direction perpendicular to the feature in the transverse cross sectional CT scan image relative to the reference mark; and determining a second angle of the direction perpendicular to the feature by adding the correcting angle to the first angle, the second angle corresponding to the angle of water flow or channel mapped to the compass coordinates.

2. The method according to claim 1, wherein selecting the arbitrary inclined plane in the CT scan image of the unoriented core comprises selecting an inclined plane corresponding to a surface of a layer within the unoriented core that is assumed to have been deposited flat on a bottom of a seabed but appearing inclined in the unoriented core due to borehole inclination angle and post-depositional structuring in the subsurface.

3. The method according to claim 1, wherein the feature includes a sedimentary feature.

4. The method according to claim 3, wherein the sedimentary feature includes a ripple, a cross bed, or a flame, or any other sedimentary feature indicating paleocurrent direction, or any combination thereof.

5. The method according to claim 1, further comprising repeating determining the first angle for a plurality of features with the core; and determining the second angle for the plurality of features within the core to obtain a plurality of second angles.

6. The method according to claim 5, further comprising determining a statistical average of the plurality of second angles, wherein the statistical average of the second angles is indicative of an average direction of flow of water in a channel in the compass map coordinates.

7. The method according to claim 1, wherein selecting an arbitrary inclined plane in a longitudinal cross sectional CT scan image of the core comprises selecting an arbitrary inclined plane in a longitudinal sectional helical CT scan image of the core.

8. The method according to claim 1, wherein determining the correcting angle to be added to the angle of the flat-bed contact plane of the core relative to the reference mark in the core comprises determining a correcting angle relative to the compass map coordinates.

9. A system for determining an orientation of a reservoir feature from an unoriented core from a subsurface, the system comprising one or more processors configured to:

read data parameters of an arbitrary inclined plane in a longitudinal or transverse cross sectional CT scan image of the unoriented core, the unoriented core being extracted from a borehole inclined relative to a vertical direction;

flatten the inclined plane by realigning all voxels within a volume of the core so as to obtain a horizontal plane in a realigned core;

read a transverse cross sectional CT scan image of the realigned core where a desired feature is present;

determine a correcting angle to be added to an angle of a flat-bed contact plane of the realigned core relative to a reference mark in the core to obtain a correct inclination angle relative to one or more compass map coordinates;

determine a first angle between a direction perpendicular to the feature in the transverse cross sectional CT scan image relative to the reference mark; and determine a second angle of the direction perpendicular to the feature by adding the correcting angle to the first angle, the second angle corresponding to the angle of water flow or channel mapped to the compass coordinates.

10. The system according to claim 9, wherein the one or more processor is configured to read an inclined plane corresponding to a surface of a layer within the unoriented core that is assumed to have been deposited flat on a bottom of a seabed but appearing inclined in the unoriented core due to borehole inclination angle and post-depositional structuring in the subsurface.

11. The system according to claim 9, wherein the feature includes a sedimentary feature.

12. The system according to claim 11, wherein the sedimentary feature includes a ripple, a cross bed, or a flame, or any other sedimentary feature indicating paleocurrent direction, or any combination thereof.

13. The system according to claim 9, wherein the one or more processors are configured to repeating determining the first angle for a plurality of features with the realigned core; and determining the second angle for the plurality of features within the realigned core to obtain a plurality of second angles.

14. The system according to claim 13, wherein the one or more processors are configured to determine a statistical average of the plurality of second angles, wherein the statistical average of the second angles is indicative of an average direction of flow of water in a channel in the compass map coordinates.

15. The system according to claim 9, wherein the CT scan image of the unoriented core is a helical CT scan image of the unoriented core.

16. The system according to claim 9, wherein the one or more processors is configured to determining the correcting angle relative to the compass map coordinates.

* * * * *